(12) United States Patent
Müller et al.

(10) Patent No.: US 7,592,452 B2
(45) Date of Patent: Sep. 22, 2009

(54) PROCESS FOR CATALYTICALLY PREPARING AROMATIC OR HETEROAROMATIC NITRILES

(75) Inventors: Nikolaus Müller, Monheim (DE); Wolfgang Mägerlein, Mannheim (DE); Matthias Beller, Ostseebad Nienhagen (DE); Thomas Schareina, Cammin (DE); Alexander Zapf, Rosenheim (DE)

(73) Assignee: SaltigoGmbH, Langenfeld (DE)

( * ) Notice: Subject to any disclaimer, the term of this patent is extended or adjusted under 35 U.S.C. 154(b) by 0 days.

(21) Appl. No.: 11/895,728

(22) Filed: Aug. 27, 2007

(65) Prior Publication Data

US 2009/0062541 A1    Mar. 5, 2009

(30) Foreign Application Priority Data

Sep. 9, 2006    (DE) .................. 10 2006 042 439

(51) Int. Cl.
   *C07D 239/24*    (2006.01)
(52) U.S. Cl. .................. 544/242; 558/343; 546/286; 248/146; 248/214; 549/474
(58) Field of Classification Search .................. 558/337, 558/343; 544/242; 546/286; 548/146, 214; 549/479, 474
See application file for complete search history.

(56) References Cited

U.S. PATENT DOCUMENTS

| 4,211,721 A | 7/1980 | Cotter |
| 4,499,025 A | 2/1985 | Davison et al. |
| 5,883,283 A | 3/1999 | Breitschuh et al. |
| 6,162,942 A | 12/2000 | Rock et al. |
| 2007/0123707 A1 | 5/2007 | Zapf et al. |

FOREIGN PATENT DOCUMENTS

| DE | 293094 | 7/1916 |
| DE | 10113976 | 9/2002 |
| DE | 102205009517 | 8/2006 |

OTHER PUBLICATIONS

Sundermeier, Mark, et al.; *Tetrahedron Letters*; 42, 2001, pp. 6707-6710.
Sundermeier, Mark, et al.; *Angew. Chem.*, 2003, 115, pp. 1700-1703.
Sundermeier, Mark, et al.; *J. Organomet. Chem.*, 2003, 684, pp. 50-55.
Wu, Jeff Xin, et. al.; *Tetrahedron Lett.* 2002, 43, pp. 387-389.
Zanon, Jacopo, et al.; *J. Am. Chem. Soc.* 2003, 125, 2890-2891.
Cristau, Henri-Jean; *Chem. Eur. J.* 2005, 11, 2483-2492.
Schareina, Thomas, et al.; *Chem. Commun.* 2004, 1388-1389.
Schareina, Thomas, et al.; *Tetrahedron Lett.* 2005, 46, 2585-2588.

*Primary Examiner*—Bernard Dentz
*Assistant Examiner*—David E Gallis
(74) *Attorney, Agent, or Firm*—Michael A. Miller

(57) ABSTRACT

The present invention relates to a process for preparing optionally substituted aromatic or heteroaromatic nitriles starting from haloaromatics. These are reacted in a copper-catalysed reaction with potassium hexacyanoferrate(II) or potassium hexacyanoferrate(III) in the presence of heteroaromatic amines.

9 Claims, No Drawings

PROCESS FOR CATALYTICALLY PREPARING AROMATIC OR HETEROAROMATIC NITRILES

BACKGROUND OF THE INVENTION

The present invention relates to a process for preparing aromatic or heteroaromatic nitriles by cyanating the corresponding aryl halides in the presence of copper catalysts and potassium hexacyanoferrate(II) ($K_4[Fe(CN)_6]$) or potassium hexacyanoferrate(III) ($K_3[Fe(CN)_6]$).

Aromatic and heteroaromatic nitriles are of industrial significance as fine chemicals, and agrochemical and pharmaceutical intermediates. Processes for their preparation are therefore of industrial significance. A known method employed on the industrial scale for preparing aromatic nitriles is the ammoxidation of substituted toluenes. This process is, however, usable practically only when the corresponding starting materials (toluenes) are available inexpensively. In addition, the ammoxidation does not succeed in the presence of oxidation-sensitive substituents in the substrate. Further technical processes for preparing benzonitriles are reactions of carboxylic acids and ammonium salts or amides by distillation with strongly water-binding substances (e.g. $P_2O_5$) and reaction of carboxylic acids or esters in the vapour phase with ammonia over an Al fixed bed at 500° C. However, such processes have disadvantages owing to the severe reaction conditions and generally cannot be applied to complexes of substituted aromatic nitriles.

Alternative inexpensive starting materials for aromatic nitriles are the corresponding aryl chlorides and bromides. However, the substitution of the halide by cyanide by known processes usually succeeds only unsatisfactorily. For example, aromatic halides react with HCN in the vapour phase at 650° C. or at 480-650° C. in the presence of a metal catalyst or metal oxide catalyst. Catalysts which accelerate the reaction of aryl halides with cyanide under milder reaction conditions are palladium complexes, nickel complexes and copper complexes. For instance, R. Breitschuh, B. Pugin, A. Indolese and V. Gisin (EP 0 787 124 B1 and U.S. Pat. No. 5,883,283) describe the preparation of substituted 3-aminobenzonitriles from the corresponding substituted 3-aminochlorobenzenes in the presence of preferably Ni complexes and stoichiometric amounts of a complexing salt. Disadvantages in this process are the use of an excess of reducing agent and the restriction of the reaction to a specific substrate class.

B. R. Cotter (U.S. Pat. No. 4,211,721) describes the positive influence of ether components from the group of 18-crown-6, polyethers, alkoxy polyethers or mixtures thereof with a molar mass of 200-25 000 as a cocatalyst on the palladium-catalysed cyanation of aryl halides.

J. B. Davison, R. J. Jasinski and P. J. Peerce-Landers (U.S. Pat. No. 4,499,025) describe the preparation of aromatic nitriles from chloroaromatics, catalysed by a group VIII metal (0) complex which is formed electrochemically. However, this procedure is exceptionally expensive in comparison to conventional batch processes.

M.-H. Rock and A. Marhold (DE 197 06 648 A1 and WO 98/37 058) describe the preparation of aromatic nitriles from chloroaromatics in the presence of a nickel catalyst and of a ketone by reaction with cyanides. The reaction can, however, be performed successfully only when the cyanide concentration is controlled strictly, since the catalyst is otherwise cyanated irreversibly. A disadvantage in this process is again the need to add a reducing agent such as zinc and the use of specific ketones as solvents.

M. Beller and co-workers describe the influence of crown ethers, diphosphine ligands and diamine ligands on the palladium-catalysed reaction of aryl halides with alkali metal cyanides (DE 101 13 976, Tetrahedron Lett. 2001, 42, 6707-10). Based on these studies, processes have been developed which are based on metered addition of acetone cyanohydrin (Angew. Chem. 2003, 115, 1700-3), trimethylsilyl cyanide (J. Organomet. Chem. 2003, 684, 50-5) or hydrocyanic acid (DE 103 22 408.4) as the cyanide donor. A disadvantage here is the use of expensive palladium catalysts and specific ligands.

A. Viauvy and M. Casado (EP 0 004 099 A1), moreover, describe the reaction of chloroaromatics to give the corresponding nitrile with stoichiometric amounts of copper cyanide and a bromide source or alkali metal cyanide or tetraalkylammonium cyanide in the presence of copper bromide and a phase transfer catalyst or copper cyanide and lithium iodide. A disadvantage here is the use of stoichiometric amounts of the transition metal.

A copper-catalysed cyanation of aryl halides has been described by Wu et al. (Tetrahedron Lett. 2002, 43, 387-389). They use 5 mol % of a copper(I) salt as a catalyst and sodium cyanide as the cyanide source. Good yields can be achieved, however, only in the reaction of reactive and expensive iodoaromatics. A further disadvantage of the process is the use of ionic liquids as the solvent, which are expensive and can be cleaned only with difficulty.

J. Zanon, A. Klapars and S. L. Buchwald (J. Am. Chem. Soc. 2003, 125, 2890-1) describe the cyanation of bromoaromatics with sodium cyanide in the presence of 10 mol % of copper(I) iodide as a catalyst and 20 mol % of potassium iodide as a cocatalyst. In addition, one equivalent of N,N'-dimethylethylenediamine is added. It is assumed that the aryl bromides are converted to the corresponding iodides as an intermediate, which are then cyanated.

In a method likewise catalysed by copper(I) iodide of Cristau et al. (Chem. Eur. J. 2005, 11, 2483-2492), 20 mol % of the 1,10-phenanthroline ligand and acetone cyanohydrin as the cyanide donor are used. Here too, potassium iodide has to be used as a cocatalyst.

A significant disadvantage of all catalytic cyanations described so far is the sometimes extremely high toxicity of the cyanating agents used, which is based on the fact that hydrocyanic acid is released on contact with water. M. Beller et al. for the first time described catalytic cyanations with the non-toxic potassium hexacyanoferrate(II) [Chem. Commun. 2004, 1388-1389]. However, a disadvantage in this process is that the reactions succeed only in conjunction with a palladium catalyst.

Moreover, T. Schareina, A. Zapf and M. Beller (Tetrahedron Lett. 2005, 46, 2585-2588) describe the cyanation of aryl bromides with Cu catalysts in the presence of the N,N'-dimethylethylenediamine ligand. Owing to the high cost of this ligand, industrial uses are unrealistic.

In summary, it remains to be emphasized that almost all transition metal-catalysed cyanations of aryl halides known to date use either expensive toxic cyanide sources or expensive catalyst systems.

SUMMARY OF THE INVENTION

It was therefore an object of the present invention to develop an improved process for cyanating haloaromatics. In particular, this process should be usable efficiently on the industrial scale and be superior to the prior art processes with regard to the catalyst costs and the toxicity of the cyanide source. Surprisingly, it has been found that a combination of copper compounds and inexpensive additives catalyses the reaction of aryl halides with non-toxic cyanide sources, for example potassium hexacyanoferrate(II) or potassium hexacyanoferrate(III).

DETAILED DESCRIPTION OF THE INVENTION

The object stated has been achieved in accordance with the claims by, in a process for catalytically preparing optionally substituted aromatic or heteroaromatic nitriles of the general formula (I)

Ar—CN                                                                  (I)

performing the reaction of the corresponding aryl halides of the general formula (II)

Ar—X                                                                    (II)

in which X is chlorine, bromine, iodine or sulphonate, preferably chlorine and bromine, more preferably bromine, and Ar is an optionally substituted aromatic or heteroaromatic radical
using potassium hexacyanoferrate(II) or potassium hexacyanoferrate(III) as a cyanide donor in the presence of copper compounds and monodentate, five- to six-membered heteroaromatic amines having one to three nitrogen atoms.

The cyanating reagent used in accordance with the invention, potassium hexacyanoferrate(II), is non-toxic, dissolves in water without decomposition and is even used in the food and drink industry, for example in the production of table salt or for the preservation of wines (Roempp Lexikon Chemie, Georg Thieme Verlag, Stuttgart/N.Y., 1999).

The copper compounds used may be known copper(I) and copper(II) compounds. Typical examples are the copper halides such as CuI, CuBr, copper carboxylates such as $Cu(OAc)_2$, copper cyanides such as CUCN, copper alkoxides such as $Cu(acac)_2$, copper aqua and copper amine complexes such as $[Cu(NH_3)_4]SO_4$, but also cationic copper compounds such as $Cu(BF_4)_2$. Preference is given to copper halides and copper(II) tetrafluoroborate.

The copper compound used should be present in the reaction mixture in a sufficient amount. The person skilled in the art will select the use amount necessary with reference to economic considerations (rapidity of the reaction, yield, material costs). In the process according to the invention, turnover values of the catalysts in the order of magnitude of at least 10 to 100 000 can be realized. Preference is given to using the copper compound in an amount of 100 ppm to 100 mol % based on the aryl halide used. Preference is given to using 1 mol % to 30 mol %.

Solvents used in the process according to the invention are generally inert organic solvents and/or water. Advantageous solvents have been found to be dipolar aprotic solvents, for example aliphatic esters or amides, heteroaromatic solvents such as 1-substituted imidazoles and mixtures thereof, especially with toluene and xylene. It is particularly advantageous to use 1-alkylimidazoles such as 1-methyl- and 1-butylimidazole.

The reaction is performed at temperatures of 20 to 220° C. In particular, reaction temperatures of 80 to 200° C., more preferably 100 to 180° C., are employed.

The reaction is normally performed at ambient pressure. However, it can also be performed under pressure, for example in an autoclave or pressure tube.

Reaction-accelerating or catalyst-stabilizing additives are added. The additives used are monodentate, five- to six-membered heteroaromatic amines having one to three nitrogen atoms. Preference is given to the use of imidazoles. The imidazoles used are alkyl- or aryl- or heteroaryl-substituted imidazoles. The alkyl, aryl or heteroaryl radicals may also be substituted. In addition, it is also possible to use di- or triimidazoles or benzimidazoles (also with heteroatom substituents in the benzofused ring). Particular preference is given to the use of alkyl-substituted imidazoles such as 1-methylimidazole, 1-ethylimidazole, 1-propyl-imidazole, 1-isopropylimidazole, 1-butylimidazole, 1-sec-butylimidazole, 1-tert-butylimidazole, 1-octylimidazole, 1-benzylimidazole, etc., 1-methylbenzimidazole, 1-ethyl-benzimidazole, 1-propylbenzimidazole, 1-isopropylbenzimidazole, 1-butylbenzimidazole, 1-sec-butylbenzimidazole, 1-octylbenzimidazole, 1-benzylbenzimidazole, etc. Very particular preference is given to the use of 1-methylimidazole and 1-butylimidazole.

The imidazoles are used generally in a ratio of 1:1 to 10 000:1 (molar ligand:catalyst ratio) relative to the catalyst. They may serve as solvents.

Under some circumstances, addition of a plurality of ligands leads to synergistic positive effects.

The cyanide sources used in the process according to the invention, potassium hexacyanoferrate(II) or potassium hexacyanoferrate(III), and the corresponding catalyst system, for example composed of a combination of a copper compound and a 1-alkylimidazole, allow significantly better results to be realized in the present reaction than with commonly known reaction systems. Compared to the prior art, the following should be seen as significant advances: 1. the use of inexpensive copper catalysts instead of expensive palladium catalysts, 2. the use of a non-toxic and safe cyanide source which can be handled with significantly lower safety precautions than conventional cyanide sources, 3. the absence of iodide additions, 4. a significantly wider substrate scope and 5. the use of significantly less expensive and industrially and commercially readily available additives instead of expensive ligand systems. Thus, a comparison of different cyanation processes (Table 3) for various substrates shows significant advantages of the process according to the invention described here over known state-of-the-art processes.

In principle, there is no restriction with regard to the use of aromatics or heteroaromatics. In particular, the Ar radical may be a $(C_6-C_{19})$-aryl radical or a $(C_3-C_{18})$-heteroaryl radical having 1, 2 or 3 heteroatoms, for example nitrogen, oxygen or sulphur, in the ring.

It is possible that the Ar radical may bear up to eight substituents, which may each independently be $(C_1-C_8)$-alkyl, $(C_3-C_8)$-cycloalkyl, $(C_2-C_8)$-alkenyl, $(C_2-C_8)$-alkynyl, $(C_7-C_{20})$-aralkyl radical, OH, O—[$(C_1-C_8)$-alkyl], OC(O)—[$(C_1-C_8)$-alkyl], O-phenyl, phenyl, $NH_2$, $NO_2$, NO, N[$(C_1-C_8)$-alkyl]$_2$, NH[$(C_1-C_8)$-alkyl], NHC(O)—[$(C_1-C_8)$-alkyl], N[$(C_1-C_8)$-alkyl]C(O)—[$(C_1-C_8)$-alkyl], SH, S-phenyl, S—[$(C_1-C_8)$-alkyl], fluorine, chlorine, $CF_3$, CN, COOH, COO—[$(C_1-C_8)$-alkyl], CONH—[$(C_1-C_8)$-alkyl], COO-phenyl, COOH-phenyl, CHO, $SO_2$—$(C_1-C_8)$-alkyl, SO—$(C_1-C_8)$-alkyl, PO-(phenyl)$_2$, PO—[$(C_1-C_8)$-alkyl]$_2$, $PO_3H_2$, PO[O—$(C_1-C_8)$-alkyl]$_2$, $SO_3H$, $SO_3M$, $SO_3$—[$(C_1-C_8)$-alkyl], Si[$(C_1-C_8)$-alkyl]$_3$, $(C_1-C_8)$-haloalkyl and $(C_1-C_8)$-acyl.

$(C_1-C_8)$-Alkyl is considered to be methyl, ethyl, n-propyl, isopropyl, n-butyl, isobutyl, sec-butyl, tert-butyl, pentyl, hexyl, heptyl or octyl, including all bonding isomers. These may be mono- or polysubstituted by $(C_1-C_8)$-alkoxy, $(C_1-C_8)$-haloalkyl, OH, halogen, $NH_2$, $NO_2$, SH, S—$(C_1-C_8)$-alkyl.

($C_2$-$C_8$)-Alkenyl is understood to mean, with the exception of methyl, a ($C_1$-$C_8$)-alkyl radical as listed above which has at least one double bond.

($C_2$-$C_8$)-Alkynyl is understood to mean, with the exception of methyl, a ($C_1$-$C_8$)-alkyl radical as listed above which has at least one triple bond.

($C_1$-$C_8$)-Acyl is understood to mean a ($C_1$-$C_8$)-alkyl radical which is bonded to the molecule via a —C=O function.

($C_3$-$C_8$)-Cycloalkyl is understood to mean cyclopropyl, cyclobutyl, cyclopentyl, cyclohexyl or cycloheptyl radicals, etc. These may be substituted by one or more halogens and/or N—, O—, P—, S-containing radicals and/or have N, O, P, S atoms in the ring, for example 1-, 2-, 3-, 4-piperidyl, 1-, 2-, 3-pyrrolidinyl, 2-, 3-tetrahydrofuryl, 2-, 3-, 4-morpholinyl. This may be mono- or polysubstituted by ($C_1$-$C_8$)-alkoxy, ($C_1$-$C_8$)-haloalkyl, OH, halogen, $NH_2$, $NO_2$, SH, S—($C_1$-$C_8$)-alkyl, ($C_1$-$C_8$)-acyl, ($C_1$-$C_8$)-alkyl.

A ($C_6$-$C_{19}$)-aryl radical is understood to mean an aromatic radical having 6 to 19 carbon atoms. In particular, these include compounds such as phenyl, naphthyl, anthryl, phenanthryl, biphenyl radicals. This may be mono- or polysubstituted by ($C_1$-$C_8$)-alkoxy, ($C_1$-$C_8$)-haloalkyl, OH, halogen, $NH_2$, $NO_2$, SH, S—($C_1$-$C_8$)-alkyl, ($C_1$-$C_8$)-acyl, ($C_1$-$C_8$)-alkyl.

A ($C_7$-$C_{20}$)-aralkyl radical is a ($C_6$-$C_{19}$)-aryl radical which is bonded to the molecule via a ($C_1$-$C_8$)-alkyl radical.

($C_1$-$C_8$)-Alkoxy is a ($C_1$-$C_8$)-alkyl radical bonded to the molecule in question via an oxygen atom.

($C_1$-$C_8$)-Haloalkyl is a ($C_1$-$C_8$)-alkyl radical substituted by one or more halogen atoms.

In the context of the invention, a ($C_3$-$C_{18}$)-heteroaryl radical denotes a five-, six- or seven-membered aromatic ring system which is composed of 3 to 18 carbon atoms and has 1, 2 or 3 heteroatoms, for example nitrogen, oxygen or sulphur, in the ring. Such heteroaromatics are considered in particular to be radicals such as 1-, 2-, 3-furyl, such as 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-imidazolyl, acridinyl, quinolinyl, phenanthridinyl, 2-, 4-, 5-, 6-pyrimidinyl. A ($C_4$-$C_{19}$)-heteroaralkyl is understood to mean a heteroaromatic system corresponding to the ($C_7$-$C_{20}$)-aralkyl radical.

Possible halogens are fluorine, chlorine, bromine and iodine.

EXAMPLES

General Procedure

In an autoclave, 1 equiv. of aryl halide or heteroaryl halide, 2 equiv. of 1-alkylimidazole, 0.1 equiv. of CuI, 0.2 equiv. of dried $K_4[Fe(CN)_6]$ (potassium hexacyanoferrate(II)), tetradecane as an internal standard for the GC analysis and a suitable amount of toluene were combined under argon and heated to 160° C. (The $K_4[Fe(CN)_6]$ was dried by heating powdered $K_4[Fe(CN)_6]\times 3H_2O$ in a vacuum of $\leq 1$ mbar to 80° C. for at least 24 hours.) After 16 hours, the reaction mixture was cooled to room temperature. Conversion and yield were determinable by means of gas chromatography. An isolation of the product took place according to the customary workup (distillation, crystallization or chromatography).

TABLE 1

Copper-catalysed cyanation with potassium hexacyanoferrate(II) in the presence of 1-alkylimidazoles.

| Example No. | Ar—X | Yield of product nitrile [%] (additive) |
|---|---|---|
| 1. | 3-Bromofuran | 49 (1-Butylimidazole) |
| 2. | 4-Bromoindole | 50 (1-Methylimidazole) |
| 3. | 1-Bromo-4-nitrobenzene | 80 (1-Butylimidazole) |
| 4. | 2-Amino-5-bromopyridine | 55 (1-Methylimidazole) |
| 5. | 2-Bromo-m-xylene | 66 (180° C.); (1-Methylimidazole) |
| 6. | 3,5-Bis(trifluoromethyl)bromobenzene | 98 (1-Butylimidazole) 68 (1-Methylimidazole, 0.05 equiv. CuI) 52 (1-Butylimidazole, 0.02 equiv. CuI) 29 (1-Butylimidazole, 0.02 equiv. CuBr) |
| 7. | 2-Bromobenzotrifluoride | 83 (1-Butylimidazole) |
| 8. | 2-Amino-3-bromo-5-fluoropyridine | 93 (1-Methylimidazole) |

TABLE 1-continued

Copper-catalysed cyanation with potassium hexacyanoferrate(II) in the presence of 1-alkylimidazoles.

| Example No. | Ar—X | Yield of product nitrile [%] (additive) |
|---|---|---|
| 9. | 5-Bromopyrimidine | 95 (1-Butylimidazole) 82 (1-Methylimidazole, 0.05 equiv. CuI) |
| 10. | 2-Bromothiazole | 99 (1-Methylimidazole) |
| 11. | 2-Bromopyridine | 100 (1-Methylimidazole) |

TABLE 2

Comparison of different cyanation reagents in the cyanation of 3,5-bis(trifluoromethyl)bromobenzene with 200 mol % of 1-butylimidazole.

| Example No. | Equiv. of cyanation reagent | Yield of 3,5-bis(trifluoromethyl)-benzonitrile [%] |
|---|---|---|
| 12. | 0.2 $K_4[Fe(CN)_6]$ (140° C.) | 77 |
| 13. | 0.2 $K_3[Fe(CN)_6]$ (120° C.) | 60 |
| 14. | 1.1 KCN (120° C.) | 66 |

TABLE 3

Comparison of different cyanation methods

| Substrate | Solvent | Temperature [° C.] | Metal precursor[1] | Additives[1] | Ligand[1] | Yield [%] |
|---|---|---|---|---|---|---|
| 5-Bromo-pyrimidine | NMP | 140 | $Pd(OAc)_2$ 0.1% | $Na_2CO_3$ 20% | dppf[2] 0.2% | 0 |
| | NMP | 140 | CuI 10% | KI 20% | DMEDA 100% | 0 |
| | Toluol | 160 | CuI 10% | — | 1-Butyl-imidazole 200% | 95 |
| 2-Bromothiazole | NMP | 140 | CuI 10% | $Na_2CO_3$ 20% KI 20% | DMEDA 100% | 0 |
| | NMP | 140 | Pd(OAc)2 0.1% | $Na_2CO_3$ 20% | dppf 0.2% | 0 |
| | 1-Methyl-imidazole | 140 | CuI 10% | — | — | 99 |
| 2-Bromopyridine | NMP | 130 | $Pd(OAc)_2$ 0.5% | $Na_2CO_3$ 20% | dppp[3] 2% | 30 |
| | NMP | 110 | $Pd(OAc)_2$ 0.5% | $Na_2CO_3$ 20% | dppf 1% | 0 |
| | NMP | 140 | $Pd(OAc)_2$ 0.5% | $Na_2CO_3$ 20% | dppf 1% | <5 |

TABLE 3-continued

Comparison of different cyanation methods

| Substrate | Solvent | Temperature [° C.] | Metal precursor[1] | Additives[1] | Ligand[1] | Yield [%] |
|---|---|---|---|---|---|---|
| | NMP | 160 | Cu(BF$_4$)$_2$*6H$_2$O 10% | Na$_2$CO$_3$ 20% KI 20% | DMEDA 100% | 0 |
| | 1-Methyl-imidazole | 140 | CuI 10% | — | — | 100 |

[1]All percentages are based on the substrate.
[2]dppf = 1,1'-bis(diphenylphosphino)ferrocene.
[3]dppp = 1,3-bis(diphenylphosphino)propane.

The invention claimed is:

1. Process for catalytically preparing optionally substituted aromatic or heteroaromatic nitriles of the general formula (I)

    Ar—CN    (I)

by reacting the corresponding aryl halides of the general formula (II)

    Ar—X    (II)

in which X is chlorine, bromine, or iodine and Ar is an optionally substituted aromatic or heteroaromatic radical,
wherein the reaction is performed in the presence of copper compounds, 1-alkylimidazoles, and a cyanide donor wherein the cyanide donor is potassium hexacyanoferrate(II) or potassium hexacyanoferrate(III).

2. Process according to claim 1, wherein the copper compounds used are copper(I) and copper(II) salts or complexes.

3. Process according to claim 1, wherein the copper compounds comprise copper halides, copper cyanides or copper (II) tetrafluoroborate.

4. Process according to claim 1, wherein in that the copper compound is used in an amount of 1 ppm to 100 mol % based on the aryl halide Ar—X used.

5. Process according to claim 1, wherein the amine is used in such an amount that the molar ratio of copper compound to amine is 1:1 to 1:10 000.

6. Process according to claim 1 wherein the reaction is effected in an inert organic solvent.

7. Process according to claim 1, wherein the reaction is performed at temperatures of 20 to 220° C.

8. Process according to claim 1, wherein Ar is a (C$_6$-C$_{19}$)-aryl radical or a (C$_3$-C$_{13}$)-heteroaryl radical having 1, 2 or 3 heteroatoms selected from the group consisting of nitrogen, oxygen and sulphur in the ring.

9. Process according to claim 1, wherein the aryl halide used is selected from the group consisting of 2-bromobenzotrifluoride, 3,5-bis(trifluoromethyl)bromobenzene, 4-bromonitrobenzene, 2-bromo-6-methylaniline, 2-amino-5-bromo-3-methylbenzoic acid, 2-amino-5-chloro-3-methylbenzoic acid, 5-bromopyrimidine, 2-bromo-m-xylene, 2-bromopyridine, 2-chloropyridine, 3-bromopyridine, 3-chloropyridine, 2-bromothiazole and 3-bromofuran.

\* \* \* \* \*